United States Patent [19]

Davis et al.

[11] Patent Number: 5,290,265

[45] Date of Patent: Mar. 1, 1994

[54] NEEDLE COVER ASSEMBLY

[75] Inventors: Richard L. Davis, Wheaton; DhuAine Davis, Jr., Batavia, both of Ill.

[73] Assignee: Davis Manufacturing Systems, Inc., Wheaton, Ill.

[21] Appl. No.: 889,510

[22] Filed: May 27, 1992

[51] Int. Cl.$^5$ .............................................. A61M 5/32
[52] U.S. Cl. ......................... 604/263; 604/192; 206/365
[58] Field of Search ................ 604/192, 197, 199, 263, 604/905; 128/919; 206/365

[56] References Cited

U.S. PATENT DOCUMENTS

| | | |
|---|---|---|
| 3,055,364 | 9/1962 | Myerson et al. . |
| 3,074,542 | 1/1963 | Myerson et al. . |
| 3,245,567 | 4/1966 | Knight ............................ 604/263 X |
| 3,523,530 | 8/1970 | Pagones et al. . |
| 4,091,811 | 5/1978 | Bates et al. . |
| 4,113,090 | 9/1978 | Carstens ............................ 206/365 |
| 4,435,177 | 3/1984 | Kuhlemann et al. . |
| 4,479,496 | 10/1984 | Hsu . |
| 4,530,697 | 7/1985 | Kuhlemann et al. . |
| 4,547,140 | 10/1985 | Davis . |
| 4,657,535 | 4/1987 | Nishimura et al. . |
| 4,676,783 | 6/1987 | Jagger et al. . |
| 4,816,024 | 3/1989 | Sitar et al. ............................ 604/192 |
| 4,840,272 | 6/1989 | Goldman ............................ 206/365 |
| 4,892,525 | 1/1990 | Hermann, Jr. et al. ............. 604/263 |
| 4,915,697 | 4/1990 | Dupont ............................... 604/192 |
| 4,921,096 | 5/1990 | McFarlane ........................ 206/349 |
| 4,938,744 | 7/1990 | Wharff et al. . |
| 4,938,745 | 7/1990 | Sagstetter ......................... 504/263 |
| 5,069,341 | 12/1991 | Barbieri et al. . |
| 5,069,669 | 12/1991 | Kole ................................... 604/198 |
| 5,088,982 | 2/1992 | Ryan . |
| 5,163,915 | 11/1992 | Holleron ............................ 604/192 |

*Primary Examiner*—C. Fred Rosenbaum
*Assistant Examiner*—Corrine Maglione
*Attorney, Agent, or Firm*—Welsh & Katz, Ltd.

[57] ABSTRACT

A needle assembly for the sterile and physical protection of a needle cannula and a method for making the needle cannula is described. A removable sealing tube is integrally attached to one end of a holder which fixedly retains the needle cannula. A removable needle protector is integrally attached to the other end of the holder. The sealing tube, holder and protector define a unitary piece which encases the needle cannula. To make the needle assembly, an insert assembly including an annular die, the needle cannula and an outer cannula is positioned in a forming cavity. The forming cavity is then filled with molten plastic which upon cooling forms the unitary piece. The forward and rearward ends of the unitary piece are then sealed.

11 Claims, 3 Drawing Sheets

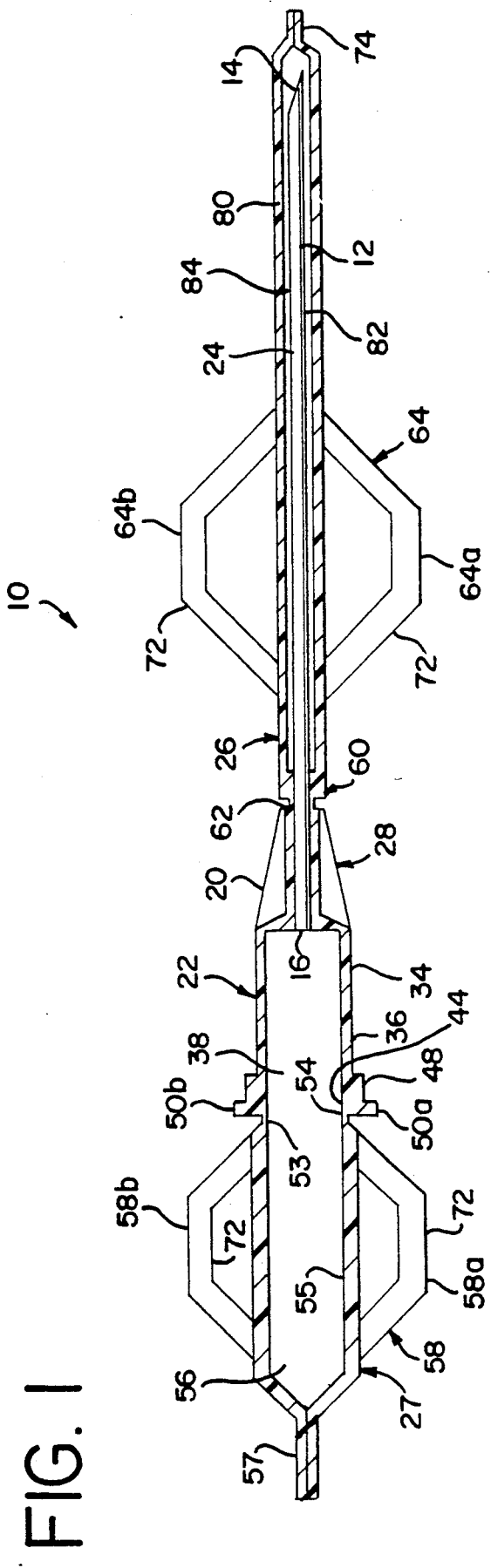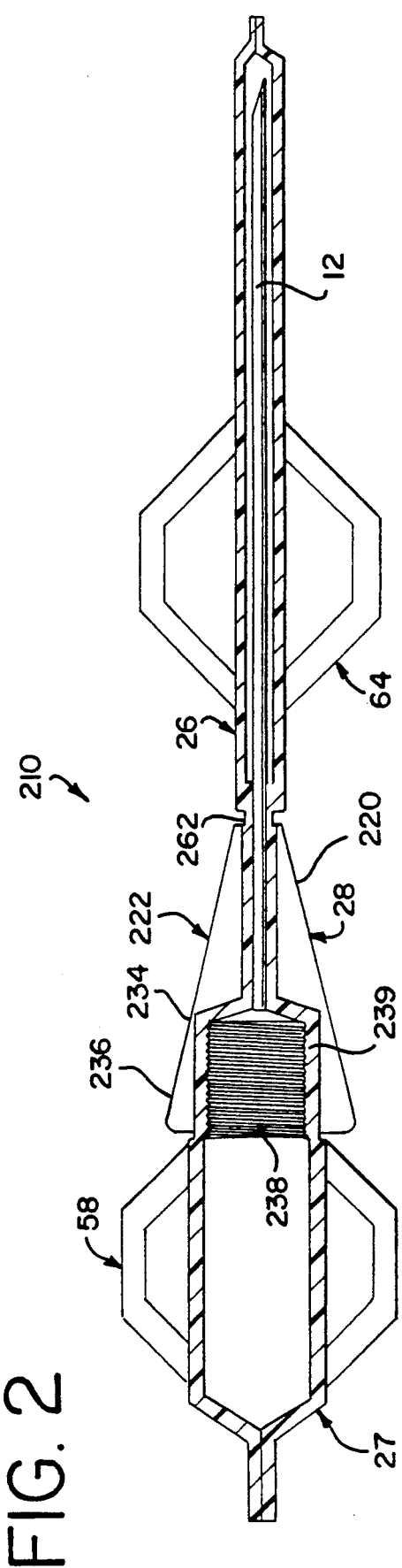

NEEDLE COVER ASSEMBLY

FIELD OF THE INVENTION

The present invention relates to medically useful needle assemblies and to a method for manufacturing needle assemblies, and specifically relates to such a needle assembly having a needle holder integrally connected to a removable needle protector and a method of manufacturing the needle assembly whereby the holder and protector are formed as portions of a unitary piece which encloses the needle cannula.

BACKGROUND OF THE INVENTION

Within the medical supplies industry, there has been a long felt need to provide an inexpensive needle assembly consisting of a sterile hypodermic needle cannula retained in a holder and enclosed in a needle protector to physically protect the needle cannula during handling. Also the holder and protection alone or in combination with other portions of the needle assembly should completely enclose the needle cannula to maintain the sterility of the needle cannula during handling.

In general, these needle assemblies should allow easy removal of the needle protector before use of the needle cannula. Also, the holder for the needle cannula should allow the user to establish a fluidly communicating connection between the needle cannula and a medical device such as a syringe.

In addition to the general requirements, users of needle cannula such as doctors and other medical personnel look for particular characteristics, such as a definitive way to determine the integrity of the sterile seal provided by the needle assembly immediately prior to removal of the protector for use, and a clean neat appearance both before and after removal of the protector. Further, due to the large number of needle cannulas employed by medical businesses, a needle assembly needs to be able to be inexpensively produced.

One general type of needle protector assembly, as disclosed in U.S. Pat. Nos. 3,523,530, 4,435,177 and 4,657,535, consists of a needle cannula having a cylindrical base or holder for retaining the needle and a hollow tubular protector which encloses an exposed portion of the needle cannula. The exposed portion extends from the holder up to and including the pointed tip. The holder and protector, however, are separately molded pieces and require an assembly step to form the needle assembly. After assembly of the separately molded pieces, the protector is bonded in a fluid-tight manner to the holder as known in the art, such as by either a heat sealing process or an adhesive. A drawback of this type of needle assembly is that the two separate molding operations and assembly step increase the cost of the needle assembly. A second drawback is that as the size of the needle cannula becomes smaller it requires greater effort and therefore more expense to establish a sealing bond between the protector and holder. Also because the bond is beneath the overlapping segment of the protector, it is difficult for medical personnel to inspect the bond prior to removal of the protector to insure the sterile seal has been maintained during handling. Finally the rearward end of the holder is open and therefore to sterilely seal the needle cannula, the holder must be bonded to a medical device or the entire needle assembly must be packaged in an additional enclosure.

A second general type of needle cover assembly, an embodiment of which is disclosed in U.S. Pat. No. 4,091,811, includes an inner sleeve which is inserted over the pointed forward end of the needle cannula. An outer sleeve retains the rearward end of the needle, extends around the inner sleeve and ends in an open end forward of the pointed end of the needle. A plug is then employed to seal the open end. This type of needle assembly also suffers the drawback of requiring three separate pieces to be molded and assembled for the needle cover to function properly. The assembly step adds expense to the manufacture of this needle cover assembly. This device also has a holder having an open rearward end and therefore requires a separate enclosure to sterilely seal the needle cannula.

Thus there is a need for a needle assembly which physically protects and preserves the sterility of the needle cannula during handling and which eliminates the separate molding operations of the component parts and an assembly of the same.

There is a further need for a needle assembly which completely encloses the needle cannula thus eliminating a separate enclosure to supply sterile protection.

There is also a need for a needle assembly which allows the user to easily determine that the sterile integrity of the needle cannula has been preserved until it becomes necessary to remove the protector.

There is an additional need for a method of manufacturing a needle assembly in which the needle cannula holder and protector are formed as a unitary piece which completely encloses the needle cannula in a single step operation. Such a method would reduce the cost of manufacturing the needle assembly and eliminate the problems associated with bonding a holder to a separate protector.

SUMMARY OF THE INVENTION

Accordingly, the present invention provides a needle assembly, having a holder and a protector for a needle cannula, which is formed as a unitary piece in a thermoinjection molding operation. With an additional sealing step, the unitary piece encases the needle cannula and provides physical and sterile protection to the cannula during handling. Also formed in the molding operation are two thin molded frangible connections one is intermediate the holder and protector which enables a user to twist the protector relative to the holder and circumferentially rupture the frangible connection, thus allowing sliding removal of the protector prior to use of the needle cannula. The other is intermediate the holder and a rear sealing tube which enables the user to remove the rear sealing tube thereby exposing the holder for connection to a medical device.

More specifically, the invention includes a needle assembly having a needle cannula including a rearward end and a pointed forward end and a holder having a carrying portion fixedly retaining the rearward end of the needle cannula. An exposed portion of the needle cannula extends from the holder and includes the forward end. The assembly also includes a needle protector having a rearward end integrally attached to the holder, and a forward sealed end. The protector encases the exposed portion of the needle cannula. The assembly further includes a rearward sealing tube integrally attached to an end of the holder opposite the protector and having a rearward sealed end. The protector, holder and sealing tube define the unitary piece which encases the needle cannula.

Also a method of producing a needle assembly having a needle cannula, a holder and a removable protector, is provided in which the needle cannula is positioned in a forming device and the forming device is filled with molten plastic which upon cooling forms a unitary piece including the rear sealing tube, holder and needle protector which encases the needle cannula.

More specifically, an insert is assembled by slidingly inserting a rearward end of a needle cannula into an axial bore defined by an annular die and sheathing an exposed portion of the needle cannula with an outer cannula. This insert is positioned in a forming cavity. The forming cavity is next filled with molten plastic which, upon cooling, forms the needle assembly having a needle holder, protector and sealing tube. A rearward open end of the sealing tube and a forward open end of the needle protector is then sealed. Thus a needle assembly may be provided which physically protects and maintains the sterility of the needle cannula and has the needle holder integrally connected to the needle protector and sealing tube to form a unitary piece.

BRIEF DESCRIPTION OF THE DRAWINGS

FIG. 1 is a longitudinal cross sectional view of a needle cover assembly according to the present invention;

FIG. 2 is a longitudinal cross sectional view of an alternate embodiment of the needle cover assembly according to the present invention;

DESCRIPTION OF THE PREFERRED EMBODIMENTS

Figure 3:
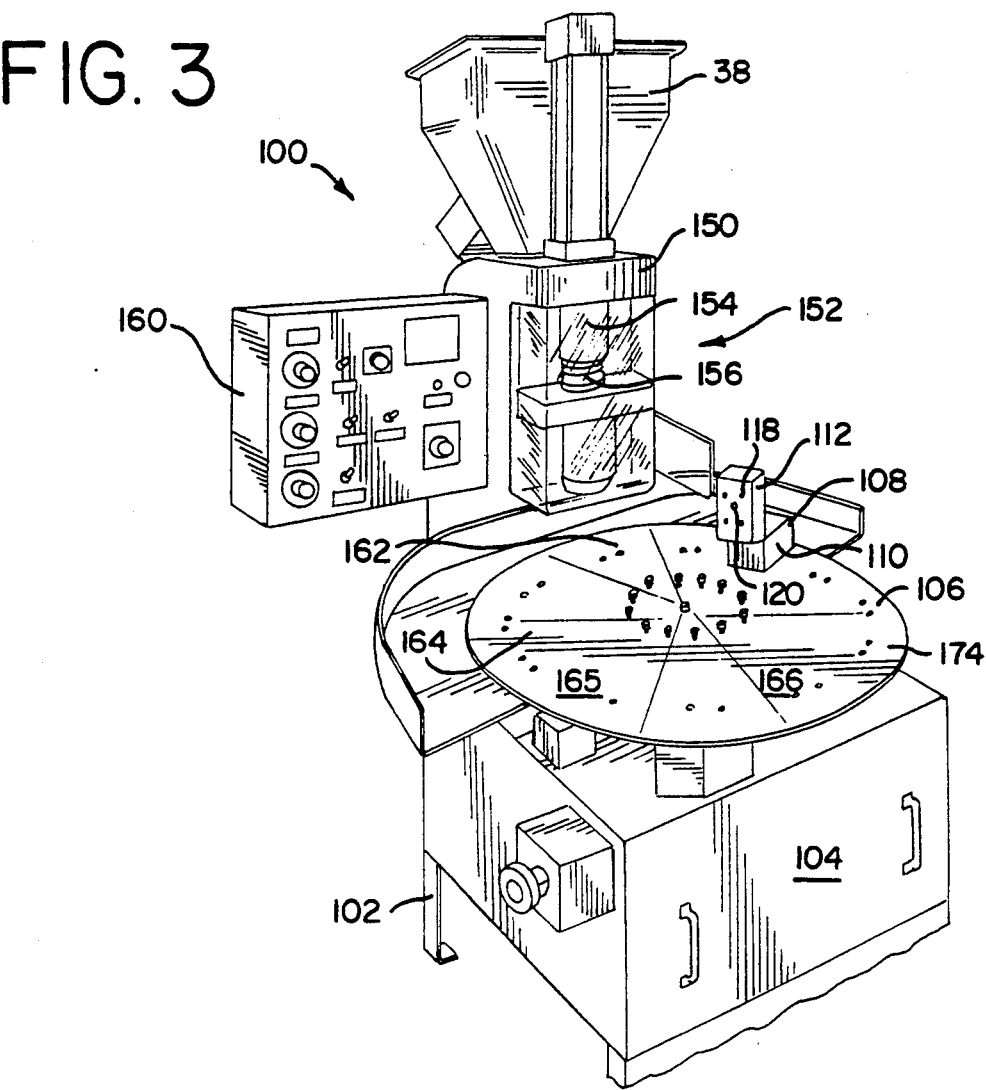
FIG. 3 is a perspective front view of an injection molding press for producing the needle cover assembly according to the present invention.

Referring to FIG. 1, the preferred embodiment of the needle and cover assembly as is contemplated herein is generally indicated at 10. The assembly 10 includes a needle cannula 12 having a pointed forward end 14 and a rearward end 16. The rearward end 16 of the needle cannula 12 passes through a carrying portion 20 of a holder 22 and is fixedly retained by the same. An exposed portion 24 of the needle cannula 12 extending forward of the holder 22 includes the pointed forward end 14. To provide sterile and physical protection to the exposed portion 24, the assembly 10 includes a needle protector indicated at 26. Integrally connected to and extending rearward from the holder 22 is the sealing tube 27 which provides sterile and physical protection to the rearward end 16 of the needle cannula 12. The protector 26 and sealing tube 27 are integrally connected to opposite ends of the holder 22 thereby defining a unitary piece 28 and are manufactured in a single thermoinjection molding step as is described below. The holder 22, protector 26 and sealing tube 27 are composed of a medically inert thermoplastic material such as polyethylene, polypropylene, or the like. One of the advantages of having the protector 26 and sealing tube 27 integrally connected to the holder 22 is that the connection eliminates any hidden bonding points; therefore, a visual inspection of the outer surface of the needle assembly supplies a definitive way of determining the sterile integrity of the needle cannula has been preserved during handling. Another one of the advantages of forming a unitary piece is that it presents a visual appearance that is clean and neat with no visible seams.

In addition to the carrying portion 20, the holder 22 has a barrel portion 34 which includes a rearward connector portion 36 defining an annular recess 38 which is shaped to conform to a fluid nozzle on a medical instrument and allow fluid communication between the nozzle and the needle cannula. In the preferred embodiment, the connector portion 36 is configured engage a nozzle of a syringe (not shown) in a fluid tight manner. Also in the preferred embodiment, the rearward end 44 of the connector portion 36 includes a radial lip 48 having a pair of integrally connected radially extending ears 50a and 50b disposed on opposite sides of the annular recess 38. The ears 50a and 50b allow the connector portion 36 to be threadingly engaged to an internally threaded annular flange such as that found on a medical syringe (not shown).

As before-mentioned, the sealing tube 27 is integrally attached to the holder 22 so as to provide sterile protection to the annular recess 38 during packaging and handling prior to use. A forward end 53 of the sealing tube 27 defines a rearward thin frangible annular portion 54. The rearward annular portion 54 is designed to facilitate removal of the sealing tube 27 by circumferentially rupturing upon twisting the sealing tube relative to the holder 22. An inner surface 55 of the sealing tube 27 defines a lumen 56. Although the inner surface 55 need not be cylindrical, the inner surface is preferably so formed to aid in manufacture of the needle assembly 10. The sealing tube 27 defines a sealed rearward end 57. The rearward end 57 may be sealed by application of a heated crimp as shown and which is described below; however, other sealing methods such as a sealing cap are also contemplated.

The sealing tube 27 may include at least one integrally attached rearward flange 58 which facilitates the handling of the assembly 10 and the twisting of the sealing tube relative to the holder 22.

Integrally connected to a forward thin frangible annular portion 62 of the holder 22 is a rearward end 60 of the needle protector 26. The forward annular portion 62 is designed to facilitate the removal of the protector 26 by circumferentially rupturing upon twisting the protector relative to the holder 22.

The protector 26 may include at least one integrally attached forward flange 64 which facilitates the handling of the assembly 10 and the twisting of the protector 26 relative to the holder 22.

The preferred embodiment of the rearward flange 58 and forward flange 64 includes a first set and a second set of wings 58a and 58b and 64a and 64b, respectively. The first set of wings 58a, 58b, lie in a common plane and are disposed on opposite sides of the sealing tube 27. Similarly, the second set of wings 64a, 64b, the wings lie in a common plane and are disposed on opposite sides of the needle cannula 12. The wings 58a, 58b and 64a, 64b are trapezoidal shaped with the base of the wings integrally attached to the sealing tube 27 and protector 26, respectively. Around the outer periphery of each of the wings 58a, 58b, 62a, 62b is a thickened rib 72. During the molding of the needle assembly 10, the ears 50a and 50b, first set of wings 58a, 58b and second set of wings 64a, 64b may be aligned to provide a tamper evident feature. Therefore, a non-aligned first set of wings 58a, 58b, second set of wings 64a, 64b, or ears 50a and 50b would indicate that the needle assembly 10 has been tampered with.

Needle protector 26 defines a forward end 74 which extends forward of the pointed forward end 14 of the needle cannula 12. Forward end 74 may be sealed by application of a heated crimp as shown and which is described below; however, other sealing methods such as a sealing cap are also contemplated. Sealing the forward end 74 of the protector 26 encases the exposed portion 24 of the needle cannula 12. An inner surface 80 of the needle protector 26 adjacently circumscribes an outer surface 82 of the exposed portion 24 of the needle cannula 12 and is dimensioned so that it provides a sliding fit with the needle cannula. Although the inner surface 80 need not be cylindrical, the inner surface is preferably so formed to aid in the manufacture of the assembly 10. In the preferred embodiment, the outer surface 82 of the exposed portion 82 of the needle cannula 12 is radially spaced from the inner surface 80 of the needle protector 26 with the outer surface 82 and inner surface 80 defining a hollow tubular clearance 84. The tubular clearance 84 reduces friction between the needle protector 26 and exposed portion 24 of the needle cannula 12 during the twisting and sliding removal of the needle protector.

Referring to FIG. 2, an alternate embodiment of the needled assembly 210 is shown. The alternate embodiment of needle assembly 212 includes the sealing tube 27 with integrally attached flange 58, the needle cannula 12 and the needle protector with integrally attached flange 64 which correspond to the previously described structure of the preferred embodiment. The alternate embodiment also includes a holder 222. The holder 222 includes a carrying portion 220; a forward thin, frangible annular portion 262 and a barrel portion 234 which includes a rearward connector portion 236 which defines an annular recess 238. Connector portion 236 has a threaded internal surface 239, which is shaped to conform to an externally threaded fluid nozzle of a dental syringe (not shown) and allow fluid communication between the nozzle and needle cannula.

Referring again to FIG. 1, to employ the preferred embodiment of the needle assembly 12, the rearward flange 58 and holder 22 are grasped and the sealing tube 27 is twisted relative to the holder thereby circumferentially rupturing the rearward annular portion 54 and exposing the connector portion 36. The sealing tube 27 is then discarded and the connector portion 36 is then threadingly engaged with a syringe. The forward flange 64 is then grasped and the protector 26 is twisted to circumferentially rupture the forward annular portion 62. The protector 26 is then slidingly removed and discarded.

Figure 4:
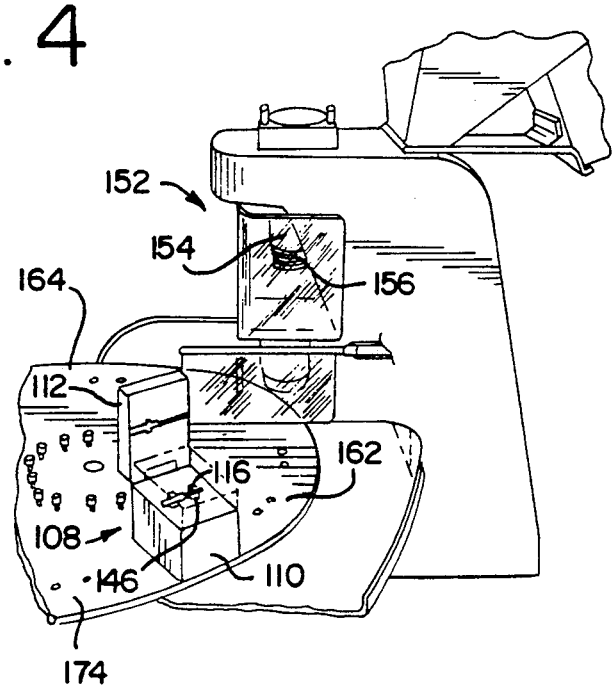
FIG. 4 is a partial perspective side view of the molding press illustrating the table and injector mechanism.
Figure 5:
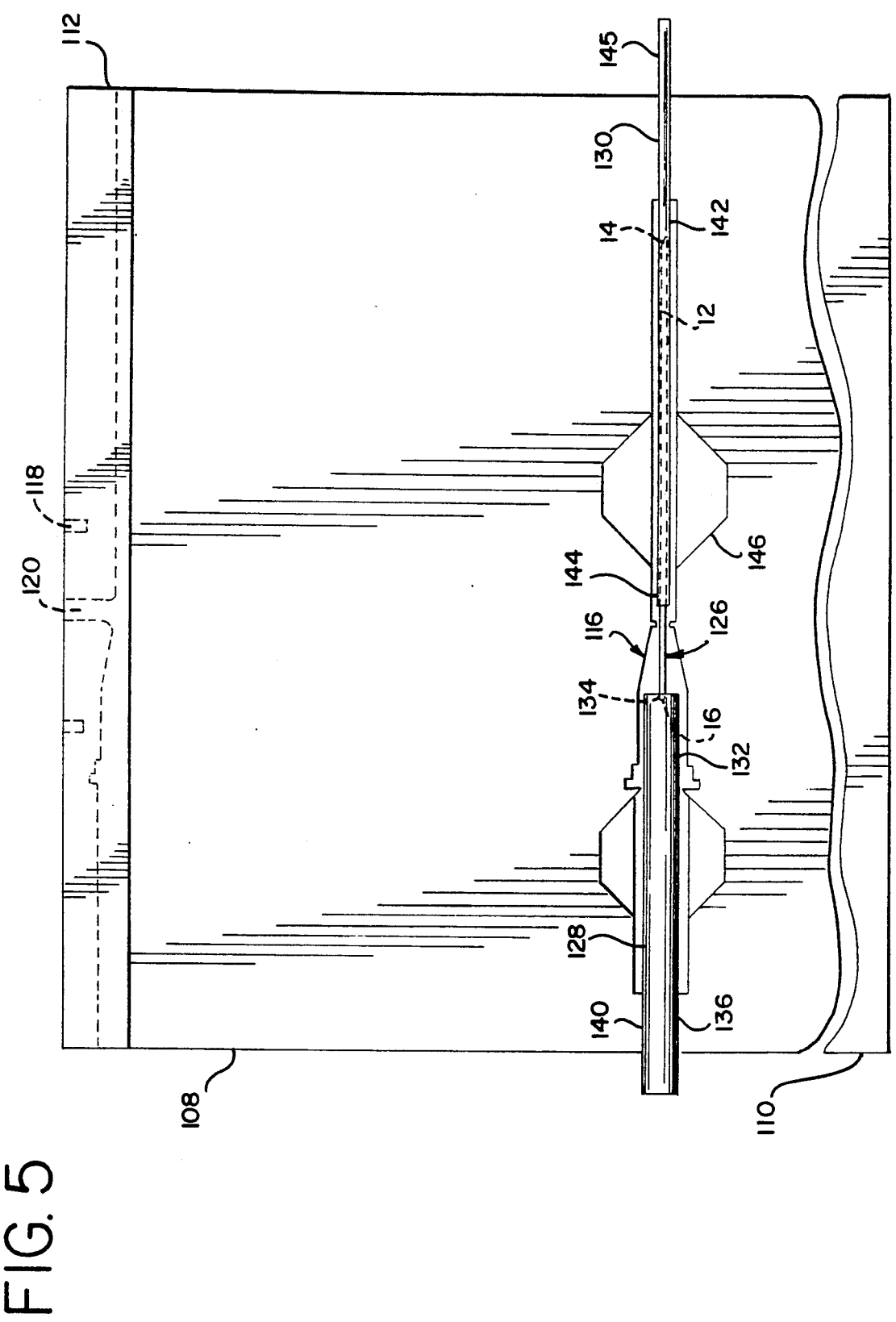
FIG. 5 is a top plan view of an insert assembly in a forming cavity of a mold block for producing the needle cover assembly according to the present invention.

Referring now to FIGS. 3-5, in order to produce a needle assembly 10 having the protector 26 and sealing tube 27 integrally connected to the holder 22 a method must be provided which results in the formation of the unitary piece 28 in a single molding operation. To this end. FIG. 3 illustrates a rotary injection molding press 100 which makes needle assemblies in accordance with the present invention, however, it is to be understood that the present method of manufacture invention is equally applicable to other types of molding processes and machinery which performs those processes. The press has an upstanding frame 102, a portion of which defines a lower, and frontally extending cabinet to house the hydraulics and electronics of the press 104.

Disposed on the press 100 is a movable platform embodied as a circular table 106. As FIG. 3 illustrates, the table 106 is rotatable in a counterclockwise direction. The table 106 mounts one or more mold blocks 108, only one of which is shown in the drawings, and transports each mold block 108 through several stations of the press 100 as described below.

As seen in FIGS. 3 and 4, each mold block 108 has a bottom 110 secured to the table 106 by a clamp or the like (not shown) and a top 112 hinged to the bottom for pivoting opening and closing movement. When the mold block 108 is open, the top 112 extends upwardly from the bottom 110. Referring to FIG. 5 fashioned in the mold block 108 is at least one forming cavity 116 adapted to form the desired needle assembly 10. The forming cavity 116 is preferably cooperatively fashioned in the top 112 and bottom 110 of the mold block 108. Each mold block 108 may contain a plurality of forming cavities 116. As shown in FIG. 2 and FIG. 5, the top 112 has aligning bores 118 and a female opening 120 which directly communicates with the cavity 116.

Referring to FIG. 5 in conjunction with FIG. 1, in order to prepare a forming cavity indicated generally at 116, for injection molding of the needle assembly 10, the needle cannula 12 which will become part of the needle assembly must be positioned within the forming cavity 116 so that during the molding of the needle assembly the needle cannula will be properly disposed within the assembly and molten plastic will be prevented from intruding into the hollow rearward end 16 and forward end 14 of the needle cannula. The preferred method of positioning the needle cannula 12 is to use an electromagnet (not shown) to place an insert assembly, generally designated at 126, in the mold block. Use of electromagnets to place inserts for thermoinjection molding is well known in the art. The insert 126 includes an annular die 128, the needle cannula 12 and an outer cannula 130. The die 128 has a forward tip 132 defining an axial bore 134. The tip 132 is positioned to extend into the forming cavity 116 and is adapted to form the lumen 56 and annular recess 38 of the needle assembly 10 during the molding. In the alternate embodiment of the needle assembly shown in FIG. 2, the surface of the tip 132 is threaded to form the threaded portion of the internal surface 239 of the connector portion 236. A rearward portion 136 of the die 128 is configured to matingly fit within a recess 140 adjoining the forming cavity 116 and extend out of the mold block 108 to insure that the insert 126 is properly positioned in the forming cavity.

To support the rearward end 16 of the needle cannula 12, the rearward end is inserted into the axial bore 134 within the forward tip 132 of the annular die 128. The depth of insertion corresponds to the desired penetration of the rearward end 16 into the annular recess 38 of the completed needle assembly 10. In the preferred embodiment, the fit between the axial bore 134 and rearward end 16 should allow sliding removal of the needle cannula 12 from the annular die 128 but prevent ingress of molten plastic into the axial bore during the molding.

Also included in the insert assembly 126 is the outer cannula 130. The inner diameter of the outer cannula 130 is dimensioned to allow the outer cannula to sheathingly slide over the needle cannula 12 to prevent the penetration of molten plastic between the outer cannula and needle cannula during the molding of the needle assembly 10. The outer cannula 130 is positioned along the needle cannula 12 to prevent the penetration of the molten plastic into the pointed forward end 14. To form the preferred embodiment of the needle assembly 10, including the tubular clearance 84 and forward thin annular portion 62 of the holder 22, the outer cannula 130 has an outer surface 142 adapted to cause the formation of the tubular clearance 84 during the molding. Also, the outer cannula 130 is disposed on the needle cannula 12 so that a rearward end 144 of the outer cannula is separated from the tip 132 of the annular die 128 cause the formation of the forward thin annular portion 62 of the holder 22. A forward end 145 of the outer cannula 130 may extend out from the mold block 108 to facilitate removal of the outer cannula after molding as is described below. After the insert assembly 126 has been positioned in the forming cavity 116, the top 112 of the mold block 108 is closed. The forming cavity 116 and insert assembly 116 constructively form a prepared mold cavity indicated generally at 146.

Referring to FIGS. 3–5 in conjunction with FIG. 1, to fill the prepared mold cavity 146 with fluid plastic, the press frame 102 has an upstanding support 150 mounting an ejector mechanism 152. The injector mechanism 152 includes a piston-like plunger 154 hydraulically driven to move downward toward the table 106 against the upward returning bias provided by coil spring 156. Housed within the injector mechanism 152 adjacent to the plunger 154 are heating elements (not shown) which receive solid plastic usually in pellet form from a bin 158 disposed above the heating elements and heat the solid plastic to a fluid state.

To transport the mold blocks 108 to and from the injector mechanism 152, the press 100 includes a table indexing mechanism (not shown) disposed substantially in the cabinet 104 and controlled from a control center apparatus 160 mounted to the support 150. The indexing mechanism sequentially rotates the table 106 to move the mold blocks 108 through five stations of the press 100 as schematically shown in FIG. 2. At a portion of the press 100 defining an inject station 162, the mold block 108, when closed, is aligned with the plunger 154 of the injector mechanism 152 for injection of liquid plastic into the prepared mold cavity 146 thereof.

Disposed at the lower end of the plunger 154 as seen in FIG. 2 is an injection nozzle (not shown) which is adapted to mate with the female opening 120 of the mold block top 112. Aligning pegs (not shown) surround the nozzle and register with the aligning bores 118 to assure proper alignment of the nozzle with the female opening 120.

To fill the prepared cavity 146 with molten plastic, the plastic is heated by the heating elements to a fluid state. Thereafter the plunger 154 is driven downward such that the nozzle registers with the female opening 120 of the closed mold block 108. Further downward movement of the plunger 154 injects the fluid plastic through the nozzle to fill the prepared mold cavity 146. By filling the prepared mold cavity 146 the molten plastic will take the shape of the unitary piece 28 which includes the holder 22, sealing tube 27 and needle protector 26 of the needle assembly 10. After injection, the plunger 154 is returned by the spring 156 and additional plastic pellets are admitted to the heating elements.

After the injection mechanism 152 has filled the prepared mold cavity 146, the table 106 is indexed by the indexing mechanism in a counterclockwise fashion as shown in FIG. 2 to transport the closed mold block 108 to a cooling station 164 as another mold block 108 is positioned in the inject station 162 for injection of plastic. As the mold block 108 progresses through the cooling station 164, the liquid plastic within the prepared mold cavity 146 solidifies to form the unitary piece 28 of the present invention. The annular die 128 (FIG. 4) is then removed from the mold block 108 thereby forming the annular recess 38 and lumen 56, and the outer cannula 130 is slidingly extracted from the mold block 108 thereby creating the hollow tubular clearance 84. At or near the end of the cooling station, the mold block 108 is manually opened to expose the molded needle assembly 10.

In the preferred method the table 106 will continue to index and transports the mold block 108 to a sealing station 165 where the open rearward end 57 of the sealing tube 27 and open forward end 74 of the protector are sealed thereby encasing the needle cannula 12. The preferred method of sealing the first end 57 and second end 74 is to apply a heat crimp using a reciprocating heat crimping mechanism (not shown) as is well known in the art. Other methods of sealing the first end 57 and second end 74 such as using sealing caps after removal of the needle assembly 10 from the mold block 108 are contemplated.

continuing to index, the table 106 transports the mold block 108 to a removal station 166 where the molded needle assembly 10 is removed from the open mold block 108. The preferred method of removing the needle assembly 10 through the use of an electromagnet (not shown) which is disposed in close proximity to the needle assembly and energized thereby attracting the needle cannula 12 which causes the removal of the needle assembly from the forming cavity 116.

As the table 106 continues to be rotated by the indexing mechanism the open mold block 108 enters the prep station 174 wherein the forming cavity 116 is prepared for injection of plastic as previously described.

An advantage of the present method is that the needle assembly 10 can be produced in a single, repetitive, low cost operation. In addition, the requirements of an assembly of separately molded parts and the bonding of component parts to produce a needle assembly, which physically protects and maintain the sterility of the needle cannula during handling, have been eliminated.

A specific embodiment of the novel needle assembly and method for making the assembly according to the present invention has been described for the purposes of illustrating the manner in which the invention may be made and used. It should be understood that implementation of other variations and modifications of the invention in its various aspects will be apparent to those skilled in the art and that the invention is not limited by the specific embodiment described. It is therefore contemplated to cover by the present invention any and all modifications, variations, or equivalents that fall within the true spirit and scope of the basic underlying principles disclosed and claimed herein.

We claim:

1. A needle assembly comprising:
   a needle cannula including a rearward end portion and an exposed portion forward of said rearward end portion, said exposed portion having a pointed forward end; and
   a longitudinally extending holder including, an integral carrying portion fixedly retaining said rearward end portion of said needle cannula and a hollow barrel portion extending rearward of said carrying portion and having a rearward end, an integral needle protection portion forward of said carrying portion, said protection portion circumscribing and extending forward about an outer surface of said exposed portion of said needle cannula including said forward end of said needle cannula, said protection portion having a forward end, a first thin frangible annular portion intermediate said carrying portion and said protection portion, first means attached to said protection portion for sealing said forward end of said protector portion, and second means attached to said barrel portion for sealing said rearward end of said barrel portion whereby said holder encases said needle cannula.

2. The assembly of claim 1 wherein said holder includes at least one first flange extending from and integrally connected to said protection portion.

3. The assembly of claim 1 wherein said second sealing means includes a sealing tube integrally attached to said rearward end of said barrel portion and having a rearward sealed end.

4. The assembly of claim 3 wherein said sealing tube includes at least one outwardly extending integrally attached flange.

5. The assembly of claim 1 wherein said barrel portion includes connector means for providing fluid communication between a nozzle on a medical instrument and said rearward end portion of said needle cannula.

6. The assembly of claim 5 wherein said connector means defines an internal annular recess, said recess being configured to conform to a fluid nozzle on a medical instrument.

7. The assembly of claim 5 wherein said connector means includes an internal surface which forms an annular recess with a portion of said internal surface being threaded.

8. The assembly of claim 1 wherein said barrel portion includes an outward extending radial lip extending about said rearward end of said barrel portion, said radial lip having at least one outward extending wing for threading engagement with the fluid nozzle.

9. The assembly of claim 1 wherein said exposed portion of said needle cannula includes an outer surface and said needle protection means portion includes an inner surface, said outer surface and said inner surface defining a tubular clearance.

10. A needle assembly comprising:

a needle cannula including a rearward end portion and an exposed portion forward of said rearward end portion, said exposed portion having a pointed forward end; and a longitudinally extending holder including, an integral carrying portion fixedly retaining said rearward end portion of said needle cannula and a hollow barrel portion extending rearward of said carrying portion and having a rearward end, an integral needle protection portion forward of said carrying portion, said protection portion circumscribing and extending forward about an outer surface of said exposed portion of said needle cannula including said forward end of said needle cannula, said protection portion having a forward end, first means attached to said protection portion for sealing said forward end of said protector portion, and second means attached to said barrel portion for sealing said rearward end of said barrel portion whereby said holder encases said needle cannula, said holder including a thin frangible annular portion intermediate said barrel portion and said second sealing means.

11. A needle assembly comprising:

a needle cannula including a rearward end portion and an exposed portion forward of said rearward end portion and having an outer surface, said exposed portion having a pointed forward end;

a longitudinally extending holder including a rearward connector portion, a forward first thin frangible annular portion and a carrying portion intermediate said first annular portion and said connector portion, said carrying portion fixedly retaining said rearward end portion of said needle cannula, said connector portion defining an internal annular recess fluidly connected to said rearward end portion of said needle cannula, said recess conforming to a fluid nozzle on a medical instrument for providing fluid communication between said nozzle and said rearward end of said needle cannula;

a needle protector having a rearward end integrally attached to said first annular portion of said holder said protector circumscribing and extending about said pointed forward end of said exposed portion of said cannula, said protector also including a sealed forward end, the inner surface of said protector and an outer surface of said cannula defining a tubular clearance;

a sealing tube having a second thin frangible annular portion which is integrally attached to a rearward end of said connector portion, said tube including a sealed rearward end; and at least one flange integrally attached to said needle protector to facilitate twisting of said needle protector relative to said holder to circumferentially rupture said first annular portion.

* * * * *